United States Patent [19]

Greatbatch

[11] 4,157,720

[45] Jun. 12, 1979

[54] CARDIAC PACEMAKER

[76] Inventor: Wilson Greatbatch, 5220 Donnington Rd., Clarence, N.Y. 14031

[21] Appl. No.: 833,920

[22] Filed: Sep. 16, 1977

[51] Int. Cl.² .............................................. A61N 1/04
[52] U.S. Cl. ................................................ 128/419 P
[58] Field of Search ........ 128/419 P, 419 PG, 419 PS

[56] References Cited

U.S. PATENT DOCUMENTS

| 3,253,595 | 5/1966 | Murphy, Jr. et al. | 128/419 P |
| 3,835,864 | 9/1974 | Rasor et al. | 128/419 P |
| 3,978,865 | 9/1976 | Trabucco | 128/419 P |
| 4,010,758 | 3/1977 | Rockland et al. | 128/419 P |
| 4,046,191 | 9/1977 | Rose | 128/419 P |

FOREIGN PATENT DOCUMENTS

507326  4/1976  U.S.S.R. ................................ 128/419 P

OTHER PUBLICATIONS

Schuder et al., "Transactions of the American Society for Artificial Internal Organs" vol. X, 1964, pp. 366–369.

*Primary Examiner*—William E. Kamm
*Attorney, Agent, or Firm*—Christel, Bean & Linihan

[57] ABSTRACT

A cardiac pacemaker including a pulse generator and an electrical source such as a battery completely enveloped in a small size housing. An electrode operatively connected to the pulse generator has a helically-shaped portion extending outwardly from the housing in fixed relation thereto. The housing is of sufficiently small size to permit the pacemaker to be implanted in conjunction with a limited thoracotomy by turning the housing to rotatively insert the electrode into the heart tissue of the patient, i.e. into the myocardium. The housing can be of electrically conducting material, insulated from the electrode, and a portion of the housing can serve as an indifferent electrode.

10 Claims, 5 Drawing Figures

CARDIAC PACEMAKER

BACKGROUND OF THE INVENTION

This invention relates to the art of electronic cardiac pacemakers, and more particularly to a new and improved electronic cardiac pacemaker of the implanted type.

Early in the development of electronic cardiac pacemakers, the pacemaker electrodes were in the form of spiral platinum-iridium metal spring coils which were inserted surgically into the patient's myocardium after exposing his heart in a full thoracotomy under general anaesthesia. This was a great surgical shock to patients, especially those in aged and sick condition, and resulted in an early mortality rate of around 10 percent. Subsequent development by Dr. William M. Chardack of the implantable, transvenous, endocardial bipolar catheter essentially eliminated the high early mortality, and at the present time some 90 percent of all pacemaker surgical procedures are performed this way.

A recent development in pacemaker surgical procedures involves a limited thoracotomy whereby a helical type electrode is placed on one end of a long plastic rod and inserted into the patient through a small incision. The rod is rotated to install or screw the electrode into the patient's myocardium whereupon the rod is removed from the installed electrode and withdrawn from the patient.

It would, therefore, be highly desirable to provide an electronic cardiac pacemaker of the implantable type which is extremely small and provided with an integral electrode whereby the entire pacemaker is installed in a patient simply by rotating or screwing the pacemaker and integral electrode into the patient's myocardium in conjunction with a limited thoracotomy.

SUMMARY OF THE INVENTION

It is, therefore, an object of this invention to provide a new and improved electronic cardiac pacemaker of the implantable type.

It is a further object of this invention to provide such a pacemaker which can be installed surgically in a patient by means of a limited thoracotomy.

It is a further object of this invention to provide such a pacemaker wherein the complete pacemaker is in the form of a single epicardial structure which is sufficiently small permitting it to be screwed into the patient's myocardium by means of a limited thoracotomy.

It is a further object of this invention to provide such an electronic pacemaker which is relatively simple in construction.

The present invention provides a cardiac pacemaker comprising a pulse generator which provides electrical pulses at the output thereof which are suitable for cardiac stimulation, a source of electrical energy connected to the pulse generator, and a housing completely enveloping the pulse generator and source. An electrode is operatively connected to the output of the pulse generator and has a helically-shaped portion extending outwardly from the housing in fixed relation thereto. The housing is of sufficiently small size to permit the pacemaker to be implanted in a patient by turning the housing to rotatively insert the electrode into the heart tissue of the patient. As a result, a complete pacemaker comprising electrical source, circuitry and electrode is provided in a single epicardial structure which is sufficiently small permitting it to be screwed into the patient's myocardium in conjunction with a limited thoracotomy.

The foregoing and additional advantages and characterizing features of the present invention will become clearly apparent upon a reading of the ensuing detailed description together with the included drawing wherein:

BRIEF DESCRIPTION OF THE DRAWING FIGURES

DETAILED DESCRIPTION OF THE ILLUSTRATED EMBODIMENTS

Figure 1:
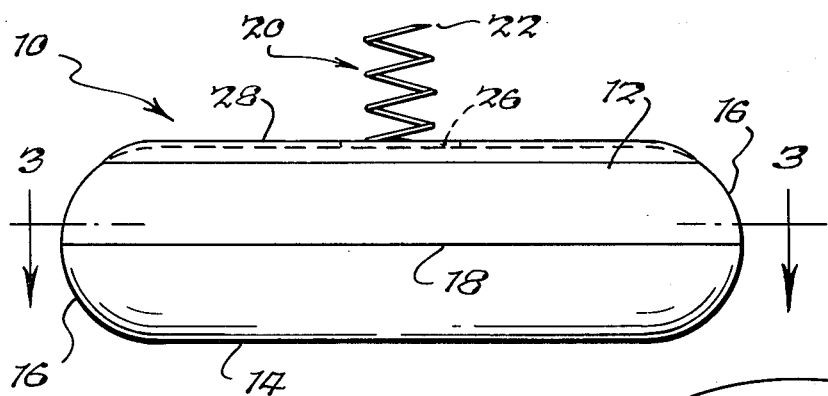
FIG. 1 is a side elevational view of a cardiac pacemaker according to the present invention.

Referring now to FIG. 1, the artificial cardiac pacemaker of the present invention comprises a housing generally designated 10 including first and second generally oppositely-directed surface portions 12 and 14, respectively, which are joined by a peripheral surface portion 16. Housing 10 is of metal, such as stainless steel or titanium, and the surface portions 12, 14 preferably are planar and of generally circular outline or configuration. The peripheral surface portion 16 is continuous and meets the surface portions 12, 14 at smooth junctions whereby the entire outer surface of housing 10 is generally smooth. The surface portions 12, 14 are disposed substantially in parallel planes which, in turn, are perpendicular to a central longitudinal axis of the housing 10. The housing 10 can comprise two generally cup-shaped halves joined such as by welding at the edges thereof to define a common juncture or seam 18 which lies in a plane substantially parallel to the planes of the surface portions 12, 14. The peripheral surface portion 16 in the structure shown is annular and of slightly convex outwardly curved shape.

The cardiac pacemaker of the present invention further comprises an electrode 20 having a helically-shaped portion extending outwardly from housing 10 in fixed relation thereto. The outer end of electrode 20 which is furthest from housing 10 terminates in a relatively sharp pointed end or tip 22. Electrode 20 has a longitudinal axis, i.e. the axis about which the helix is generated, and electrode 20 is disposed so that this axis is substantially coincident with an axis of rotation of housing 10. In particular, the longitudinal axis of helical electrode 20 is substantially coincident with the central longitudinal axis of housing 10 which is perpendicular to the surface portions 12, 14. In the cardiac pacemaker shown, electrode 20 extends from the housing surface portion 12, is located generally centrally of housing portion 12, and is disposed so that the longitudinal axis thereof is substantially perpendicular to the plane of housing portion 12. The end of electrode 20 opposite the outer end 22 preferably extends through the wall of housing portion 12 to the interior of housing 10 for making electrical connection to the pacemaker circuitry in a manner which will be described. In this regard, the portion of electrode 20 extending through the wall of housing portion 12 is sealed therein and insulated from the housing by electrical insulating means designated 26 which is between the electrode 20 and the housing surface portion 12. In particular, housing portion 12 can be provided with an opening or aperture for receiving the portion of electrode 20 which opening is filled with glass or equivalent material which serves to both insulate electrode 20 from housing 10 and to provide an hermetic between electrode 20 and housing 10. In addition, the insulating seal 26 provides a mechanical connection of electrode 20 to housing 10 of sufficient strength that electrode 20 is fixed to housing 10. Also, in the cardiac pacemaker shown the housing surface portion 12 is provided with a coating or layer 28 of electrically insulating material which can be an epoxy material or an epoxy-silicone material for a purpose to be described.

Figure 3:
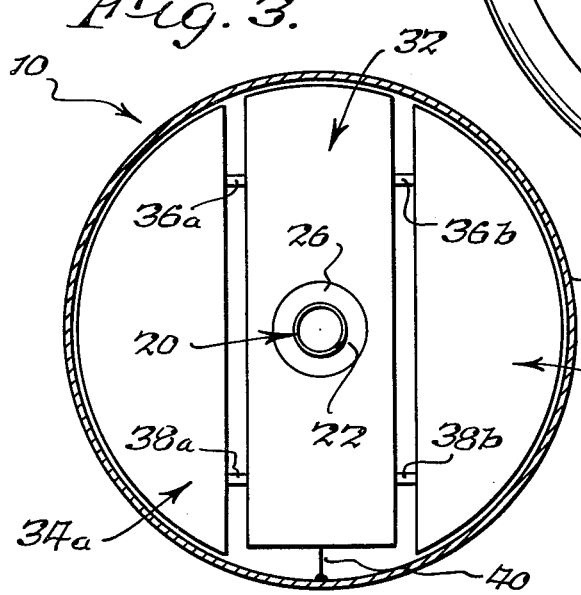
FIG. 3 is a sectional view taken about on line 3—3 of FIG. 1.

The cardiac pacemaker according to the present invention further comprises a pulse generator shown diagrammatically at 32 in FIG. 3 having an input and an output and providing output pulses suitable for cardiac stimulation. A source of electrical energy connected to the input of pulse generator 32 which source is in the form of two battery cells designated 34a and 34b in FIG. 3. The pulse generator and source of electrical energy are completely enveloped in housing 10. Pulse generator 32 can be of various forms well known to those skilled in the art so that a detailed description thereof is believed to be unnecessary. Suffice it to say, pulse generator 32 derives electrical energy from cells 34a, 34b and provides output pulses precisely controlled as to amplitude, pulse width and frequency suitable for cardiac stimulation. Detailed descriptions of various types of pulse generators for cardiac pacemakers are found in U.S. Pat. Nos. 3,870,050, 3,618,615 and 3,508,167 to mention just a few. The battery cells 34a and 34b can be lithium-iodine cells commercially available from Wilson Greatbatch Ltd. of Clarence, New York. In the pacemaker shown, the battery cells 34a, 34b are of generally semi-circular configuration so as to fit snugly within corresponding substantially semi-circular portions of the interior of housing 10. The pulse generator 32, in the form of an electronics module, is positioned between the battery cells 34a, 34b and the positive and negative terminals 36 and 38 of the corresponding cells are connected to the pulse generator 32 in appropriate manner. The terminals 36, 38 being relatively rigid also can provide some mechanical support and spacing for the electronics module 32. In the cardiac pacemaker shown, output pulses from pulse generator 32 are electrically connected to the helical electrode 20, the connection being provided in an appropriate manner such as by a short lead (not shown) from the module 32 welded to the innermost end of electrode 20. The output of pulse generator 32 also is connected electrically such as by a lead 40 to the housing 10 which being of electrically conducting material thereby can serve as an electrode. In particular, the portion of housing 10 not covered by the insulating layer 28 which contacts the patient's body will serve as an indifferent electrode.

The overall size of housing 10 must be sufficiently small so that it can be manually screwed into the patient's heart tissue during surgery and by means of a limited thoracotomy. In this connection, the overall dimension or diameter of housing 10 should be less than about 25 millimeters and the thickness, i.e. the distance between housing surface portions 12 and 14, should be less than about 10 millimeters. The size of electrode 20 could for example be of wire about 0.010" D, the coil having a major diameter of perhaps 0.175" and extending perhaps ⅛" from surface 28.

Figure 2:
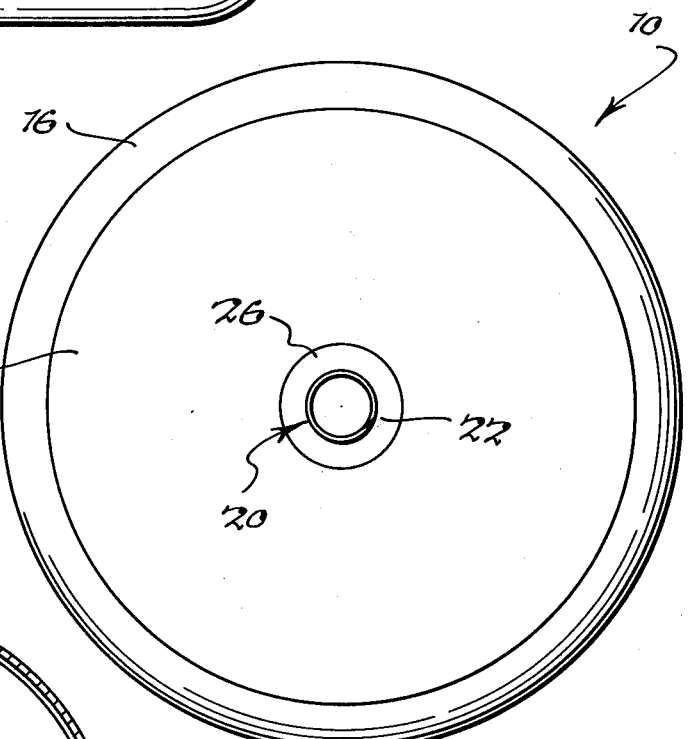
FIG. 2 is a plan view of the cardiac pacemaker of FIG. 1.
Figure 4:
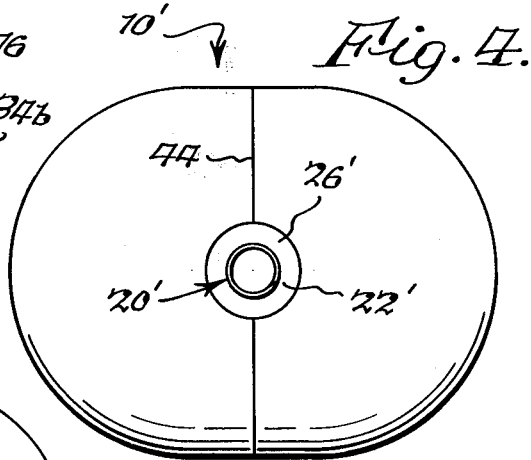
FIG. 4 is a plan view of a cardiac pacemaker according to another embodiment of the present invention.

FIG. 4 illustrates a cardiac pacemaker including a housing 10' according to another embodiment of the present invention. Housing 10' is of generally the same overall size and shape as housing 10 in the embodiment of FIGS. 1–3, but in this embodiment the two housing portions are joined such as by welding along the edges defining a seam 44 which is disposed in a plane perpendicular to the planes of the oppositely directed flat surfaces of the housing and which is generally coincident with the longitudinal axis of the helical electrode 20'. As in the embodiment of FIGS. 1–3, the inner end of helical electrode 20' is fixed in an insulating means 26' providing an hermetic seal between electrode 20' and casing 10'. In the present embodiment the seal 26' is adjacent a portion of the seam 44.

Figure 5:
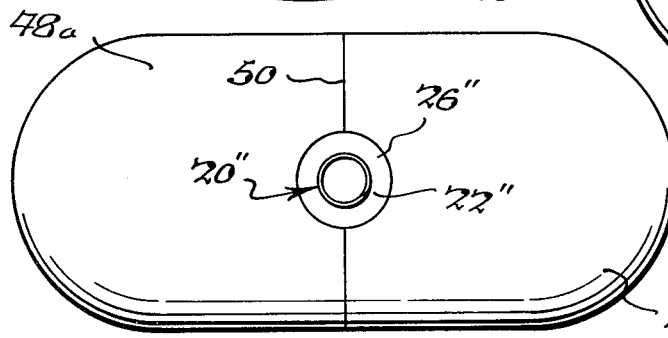
FIG. 5 is a plan view of a cardiac pacemaker according to another embodiment of the present invention.

FIG. 5 shows a cardiac pacemaker having a housing 10" according to another embodiment of the present invention. In the pacemaker of FIG. 5, the housing 10" is provided by the two casings of a pair of battery cells 48a and 48b. The battery cells 48 can be identical to the battery cells 34a and 34b in the embodiments of FIGS. 1–3, i.e. lithium-iodine cells, and in this particular arrangement the casings would be extended in the region of the lids to provide room to accomodate the electronic modules. In other words, each casing would extend out beyond the lid to define a recessed region, and when the two batteries are placed end-to-end, a hollow interior region is defined within the extended casing portions and between the lids. By virtue of this arrangement there is only a single thickness of casing, i.e. only the casing of the battery cell, not two thicknesses, i.e. one for the battery cell and one for the housing 10, as in the embodiment of FIGS. 1–4. The two battery cells 48a, 48b are joined end-to-end such as by welding at the lid ends thereof defining a peripheral seam 50. The helical electrode 20" extends therefrom in a manner such that the longitudinal axis of the electrode 20" is perpendicular to opposed flat surfaces of the resulting housing as in the embodiment of FIG. 4. The innermost end of electrode 20' is sealed in insulating material 26" which is adjacent a portion of the seam 50.

The cardiac pacemaker of the present invention is installed surgically in a patient by means of a limited thoracotomy. The pacemaker is brought into proximity with the exposed heart tissue and is turned or rotated about the axis of housing 10 to rotatively insert electrode 20 into the heart wall of the patient, i.e. the myocardium. Seal 26 is of sufficient strength to maintain electrode 20 in fixed relation to casing 10. Thus electrode 20, which is the negative electrode of the pacemaker, is connected into the heart tissue of the patient, and the portion of the housing 10 including the insulating layer 28 is adjacent or in contact with the heart tissue. The remaining portion of the housing, in particular surface 14, will contact neighboring tissue and serves as the indifferent or positive electrode. The environment to which this portion of the housing exposed will be saline fluid or tissue saturated with saline fluid thereby providing more than adequate electrical conduction. The entire pacemaker structure is held in place by the combination of electrode 20 being inserted in the heart tissue and neighboring tissue serving to support the structure. Once installed, the pacemaker supplies electrical pulses from pulse generator 32 through electrode 20 to the patient's heart, the stimulating pulses being controlled as to width, interval and frequency in a known manner.

It is therefore apparent that the present invention accomplishes its intended objects. While a single embodiment of the present invention has been described in detail, this is for the purpose of illustration, not limitation.

I claim:

1. A cardiac pacemaker comprising:
   (a) a pulse generator having an output and providing output electrical pulses suitable for cardiac stimulation;
   (b) a source of electrical energy connected to said pulse generator;
   (c) a housing completely enveloping said pulse generator and source, said housing including first and second generally oppositely-directed surface portions meeting in a peripheral portion, said housing having at least one axis extending through said surface portions about which said housing is turnable;
   (d) a stimulating electrode operatively connected to said pulse generator output and having a helically shaped portion extending outwardly from said first surface portion of said housing in fixed relation thereto and in a direction substantially along said housing axis, said helically shaped portion having a cross-sectional dimension substantially smaller than the cross-sectional dimension of said housing measured in a direction substantially perpendicular to said axis;
   (e) said pacemaker being implanted in a patient by turning said housing about said axis to rotatively insert said electrode into the heart tissue of the patient until said first surface portion of said housing is substantially in contact with the heart tissue, said second surface portion of said housing contacting neighboring body tissue when said pacemaker is implanted;
   (f) said pacemaker being held in place by the combination of the insertion of said electrode in the heart tissue and supporting contact between said housing second surface portion and the neighboring body tissue;
   (g) another electrode on said housing electrically coupled to said pulse generator and adapted to contact the neighboring body tissue of the patient; and
   (h) electrical insulating means operatively associated with said housing for insulating said stimulating electrode from said other electrode.

2. A cardiac pacemaker according to claim 1, wherein said electrode has an axis of rotation substantially coincident with said housing axis.

3. A cardiac pacemaker according to claim 2, wherein the dimension of said housing measured substantially parallel to said axis of rotation is smaller than the dimension of said housing measured substantially perpendicular to said axis of rotation.

4. A cardiac pacemaker according to claim 3, wherein said dimension measured substantially parallel to said axis is less than one-half said dimension measured substantially perpendicular to said axis.

5. A cardiac pacemaker according to claim 1, wherein said electrode extends from said first surface portion generally centrally thereof.

6. A cardiac pacemaker according to claim 5, wherein said first and second surface portions both are generally circular in shape.

7. A cardiac pacemaker according to claim 1, wherein said housing is of metal and said electrical insulating means is between said electrode and said first surface portion whereby said second surface portion serves as said other electrode.

8. A cardiac pacemaker according to claim 7, wherein said insulating means is coextensive with said first surface portion and said pulse generator is coupled electrically to said housing second portion whereby said second surface portion of said housing serves as said other electrode.

9. A cardiac pacemaker according to claim 1, wherein each of said housing surface portions is substantially smooth and continuous.

10. A cardiac pacemaker according to claim 1, wherein said electrical insulating means is operatively associated with said first housing surface portion and said second housing surface portion is electrically conductive and further including electrical conductivity means operatively associated with said second housing surface portion and operatively connected to said pulse generator whereby said second housing surface portion serves as said other electrode.

* * * * *